US012648526B2

(12) United States Patent
Cao et al.

(10) Patent No.: US 12,648,526 B2
(45) Date of Patent: Jun. 9, 2026

(54) THREE-DIMENSIONAL PLANT GROWTH LIGHTING SYSTEM

(71) Applicant: Shinegrow (Xiamen) Lighting Technology Co., LTD., Fujian (CN)

(72) Inventors: Liangliang Cao, Fujian (CN); Fuxing Lu, Fujian (CN)

(73) Assignee: Shinegrow (Xiamen) Lighting Technology Co., LTD., Xiamen (CN)

( * ) Notice: Subject to any disclaimer, the term of this patent is extended or adjusted under 35 U.S.C. 154(b) by 444 days.

(21) Appl. No.: 18/129,117

(22) Filed: Mar. 31, 2023

(65) Prior Publication Data

US 2024/0206405 A1 Jun. 27, 2024

(30) Foreign Application Priority Data

Dec. 22, 2022 (CN) .......................... 202211657240.X

(51) Int. Cl.

| | |
|---|---|
| *A01G 7/04* | (2006.01) |
| *A01G 9/24* | (2006.01) |
| *F21V 23/04* | (2006.01) |
| *H05B 45/22* | (2020.01) |
| *H05B 47/115* | (2020.01) |

(Continued)

(52) U.S. Cl.
CPC .............. *A01G 7/045* (2013.01); *A01G 9/249* (2019.05); *F21V 23/0457* (2013.01); *F21V 23/0471* (2013.01); *H05B 45/22* (2020.01); *H05B 47/115* (2020.01); *H05B 47/155* (2020.01); *F21Y 2107/50* (2016.08); *F21Y 2115/10* (2016.08); *G01N 33/004* (2013.01)

(58) Field of Classification Search
CPC .......... A01G 7/045; A01G 9/249; A01G 7/04; A01G 9/20; A01G 9/26; A01G 7/02; F21Y 2107/50
See application file for complete search history.

(56) References Cited

U.S. PATENT DOCUMENTS 8,299,445 B2* 10/2012 Yamada ................. A01G 7/045
                                                 250/455.11
9,618,178 B1 4/2017 Chappell
(Continued)

FOREIGN PATENT DOCUMENTS

| CN | 106922414 A | 7/2017 |
|---|---|---|
| CN | 108713485 A | 10/2018 |

OTHER PUBLICATIONS

Yin Wu, "Introduction to Agricultural Internet of Things(1st Edition)", Oct. 2021, cover page + p. 96, Xi'an University of Electronic Science and Technology Press, China. (www.xduph.com), Oct. 2021.

*Primary Examiner* — Trinh T Nguyen
(74) *Attorney, Agent, or Firm* — Bruce Stone LLP; Joseph A. Bruce

(57) ABSTRACT

A three-dimensional (3D) plant growth lighting system includes a top lighting module, a lateral lighting module and a bottom lighting module. The top lighting module is disposed on the top of a plant chamber and the plant chamber contains a plant. The lateral lighting module is disposed on one side of the plant chamber. The bottom lighting module is disposed on a bottom of the plant chamber. The controller is connected to the top lighting module, the lateral lighting module and the bottom lighting module so as to control the top lighting module, the lateral lighting module and the bottom lighting module.

5 Claims, 7 Drawing Sheets

(51) Int. Cl.
| | |
|---|---|
| *H05B 47/155* | (2020.01) |
| *F21Y 107/50* | (2016.01) |
| *F21Y 115/10* | (2016.01) |
| *G01N 33/00* | (2006.01) |

(56) References Cited

U.S. PATENT DOCUMENTS

| | | |
|---|---|---|
| 10,517,226 B2 | 12/2019 | Lee |
| 2010/0287830 A1 | 11/2010 | Chen |
| 2015/0319933 A1* | 11/2015 | Li .......................... A01G 22/00 47/58.1 LS |
| 2019/0008096 A1 | 1/2019 | Lee |
| 2020/0344965 A1 | 11/2020 | Song |
| 2020/0390039 A1* | 12/2020 | Sulejmani ................ A01H 6/28 |
| 2021/0259163 A1* | 8/2021 | Marder-Eppstein ..... A01G 9/26 |
| 2021/0360867 A1* | 11/2021 | Goettle .................. A01G 7/045 |
| 2021/0400885 A1* | 12/2021 | Ouammi ................ A01G 9/241 |
| 2022/0287246 A1* | 9/2022 | Westlind ................ A01G 7/045 |
| 2023/0003369 A1* | 1/2023 | Goettle ................... F21V 14/02 |

* cited by examiner

THREE-DIMENSIONAL PLANT GROWTH LIGHTING SYSTEM

BACKGROUND OF THE INVENTION

1. Field of the Invention

The present invention relates to a plant growth lighting system, in particular to a three-dimensional (3D) plant growth lighting system.

2. Description of the Prior Art

Nowadays, due to rapid development of agriculture, the demand for plant growth lighting systems is gradually increasing. The lighting devices of most currently available plant growth lighting systems are arranged above the plants.

However, the back sides of the leaves and stems of plants can also photosynthesize, and the lights emitted by the lighting devices of a currently available plant growth lighting system cannot irradiate the back sides of leaves and stems of the plants.

In addition, the lights emitted by the lighting devices of the currently available plant growth lighting system can only irradiate the leaves on the top of the plants, while other leaves blocked by the top leaves of the plants cannot effectively photosynthesize. Therefore, the currently available plant growth lighting system cannot effectively optimize the effect of photosynthesis.

SUMMARY OF THE INVENTION

One embodiment of the present invention provides a three-dimensional (3D) plant growth lighting system, which includes a top lighting module, a lateral lighting module and a bottom lighting module. The top lighting module is disposed on the top of a plant chamber and the plant chamber contains a plant. The lateral lighting module is disposed on one side of the plant chamber. The bottom lighting module is disposed on a bottom of the plant chamber. The controller is connected to the top lighting module, the lateral lighting module and the bottom lighting module so as to control the top lighting module, the lateral lighting module and the bottom lighting module.

In one embodiment, the 3D plant growth lighting system further includes a height sensor connected to the controller. The height sensor detects the height of the plant in order to generate a height signal and the controller adjusts the lighting range of the lateral lighting module according to the height signal.

In one embodiment, the 3D plant growth lighting system further includes a database connected to the controller and saving a plurality of light formulas corresponding to a plurality of plant species respectively.

In one embodiment, the controller downloads the light formula corresponding to the plant from the database and generates an intelligent control signal according to the light formula in order to control the top lighting module, the lateral lighting module and the bottom lighting module.

In one embodiment, the 3D plant growth lighting system further includes a carbon dioxide (CO2) module connected to the controller. The CO2 module includes a CO2 generator and a CO2 sensor. The CO2 sensor detects the CO2 concentration of the plant chamber and generate a CO2 concentration signal.

In one embodiment, the controller controls the CO2 generator according to the CO2 concentration signal.

In one embodiment, the 3D plant growth lighting system further includes an illuminance sensor connected to the controller and detecting the illuminance of the plant chamber in order to generate an illuminance signal.

In one embodiment, the 3D plant growth lighting system further includes a spectrum sensor connected to the controller and detecting the spectrum of the light in the plant chamber so as to generate a spectrum signal.

In one embodiment, the controller downloads the light formula corresponding to the plant from the database. Then, the controller compares the light formula with the CO2 concentration signal, the illuminance signal and the spectrum signal to generate an intelligent control signal so as to control one or more of the CO2 generator, the top lighting module, the lateral lighting module and the bottom lighting module.

In one embodiment, the top lighting module, the lateral lighting module and the bottom lighting module are light-emitting diode (LED) lighting modules.

The 3D plant growth lighting system in accordance with the embodiments of the present invention may have the following advantages:

(1) In one embodiment of the present invention, the 3D plant growth lighting system has a top lighting module, a lateral lighting module and a bottom lighting module. The lights emitted by the above three lighting modules can irradiate the front sides, the back sides and the stems of the plant. Thus, the 3D plant growth lighting system can effectively enhance the photosynthesis of the plant in order to optimize the effect of photosynthesis.

(2) In one embodiment of the present invention, the 3D plant growth lighting system has the top lighting module, the lateral lighting module and the bottom lighting module. The lights emitted by the above three lighting modules can irradiate most of the leaves of the plant. Therefore, the 3D plant growth lighting system can further enhance the photosynthesis of the plant so order to further optimize the effect of photosynthesis.

(3) In one embodiment of the present invention, the 3D plant growth lighting system includes a motor module, a lifting mechanism and a height sensor. The height sensor can detect the height of the plant in order to generate a height signal. In this way, the controller can control the lifting mechanism to adjust the height of the height sensor and the lighting range of the lateral lighting module according to the height signal. Accordingly, the lighting range of the lateral lighting module can be changed according to the height of the plant, which not only can further optimize the effect of the photosynthesis, but also can save more energy.

(4) In one embodiment of the present invention, the 3D plant growth lighting system includes a database saving a plurality of light formulas. Each light formula is corresponding to one plant species, so the light formula can satisfy the growth requirements of the plant. Thus, the controller not only can adjust the brightness, spectrum and color temperature of each of the top lighting module, lateral lighting module and bottom lighting module according to the light formula, but also can adjust the CO2 concentration according to the light formula. In this way, the 3D plant growth lighting system can create an environment capable of satisfying the growth requirements of the plant.

(5) In one embodiment of the present invention, the 3D plant growth lighting system includes the database saving the light formulas. Each light formula is corresponding to one plant species, and includes the illumi-
nance parameters, spectrum parameters and CO2 con-
centration parameters of different growth stages of the
plant. Accordingly, the controller not only can precisely
adjust the lights emitted by the top lighting module,
lateral lighting module and the bottom lighting module,
but also can accurately adjust the CO2 generated by the
CO2 generator. As a result, the environment created by
the plant growth lighting system can completely con-
form to the requirements of different growth stages of
the plant.

These and other objectives of the present invention will
no doubt become obvious to those of ordinary skill in the art
after reading the following detailed description of the pre-
ferred embodiment that is illustrated in the various figures
and drawings.

BRIEF DESCRIPTION OF THE DRAWINGS

The present invention will become more fully understood
from the detailed description given herein below and the
accompanying drawings which are given by way of illus-
tration only, and thus are not limitative of the present
invention and wherein.

DETAILED DESCRIPTION

In the following detailed description, for purposes of
explanation, numerous specific details are set forth in order
to provide a thorough understanding of the disclosed
embodiments. It will be apparent, however, that one or more
embodiments may be practiced without these specific
details. In other instances, well-known structures and
devices are schematically shown in order to simplify the
drawing. It should be understood that, when it is described
that an element is "coupled" or "connected" to another
element, the element may be "directly coupled" or "directly
connected" to the other element or "coupled" or "connected"
to the other element through a third element. In contrast, it
should be understood that, when it is described that an
element is "directly coupled" or "directly connected" to
another element, there are no intervening elements.

Figure 1:
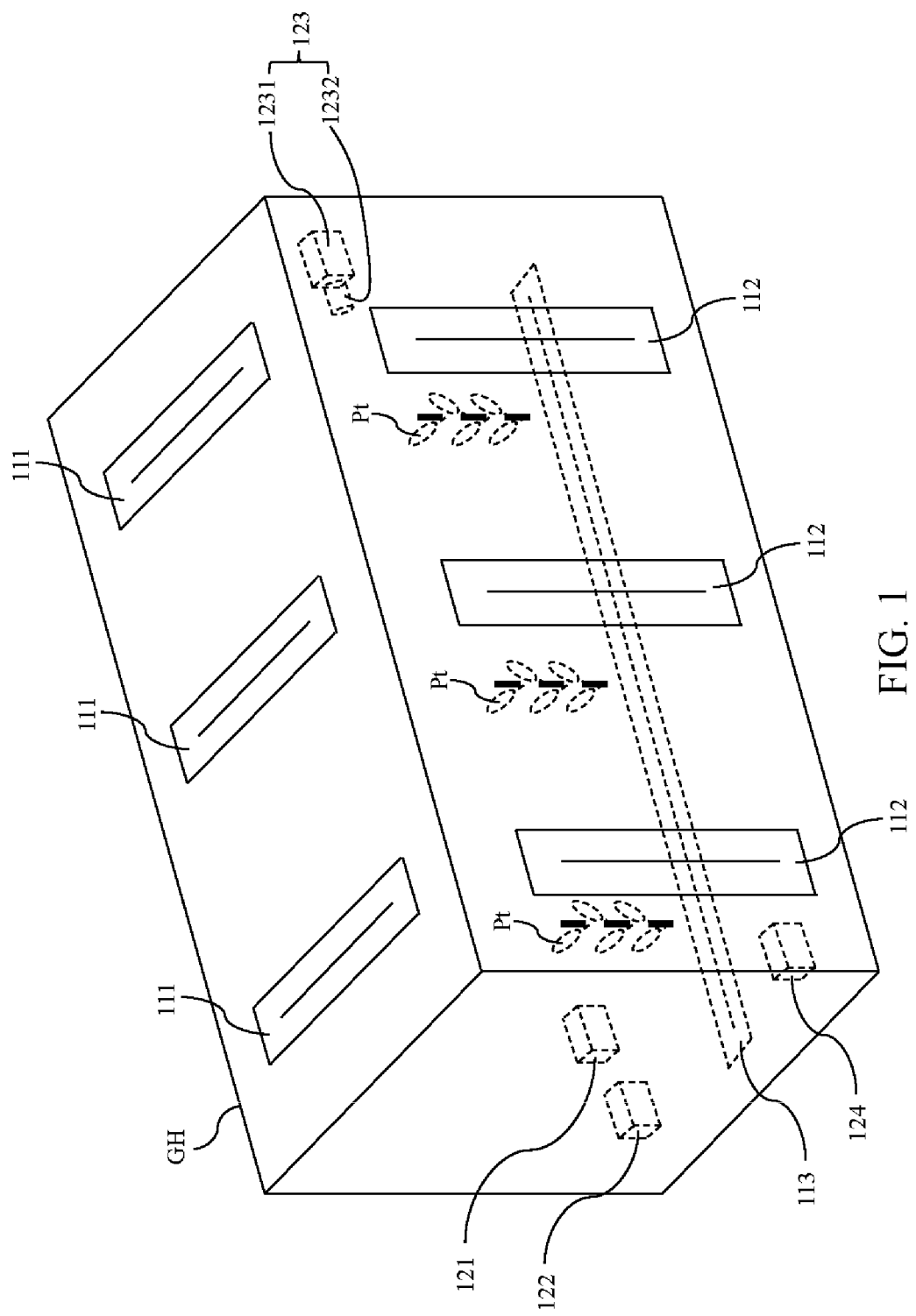
FIG. 1 is a schematic view for illustrating a structure of
a 3D plant growth lighting system in accordance with one
embodiment of the present invention.
Figure 2:
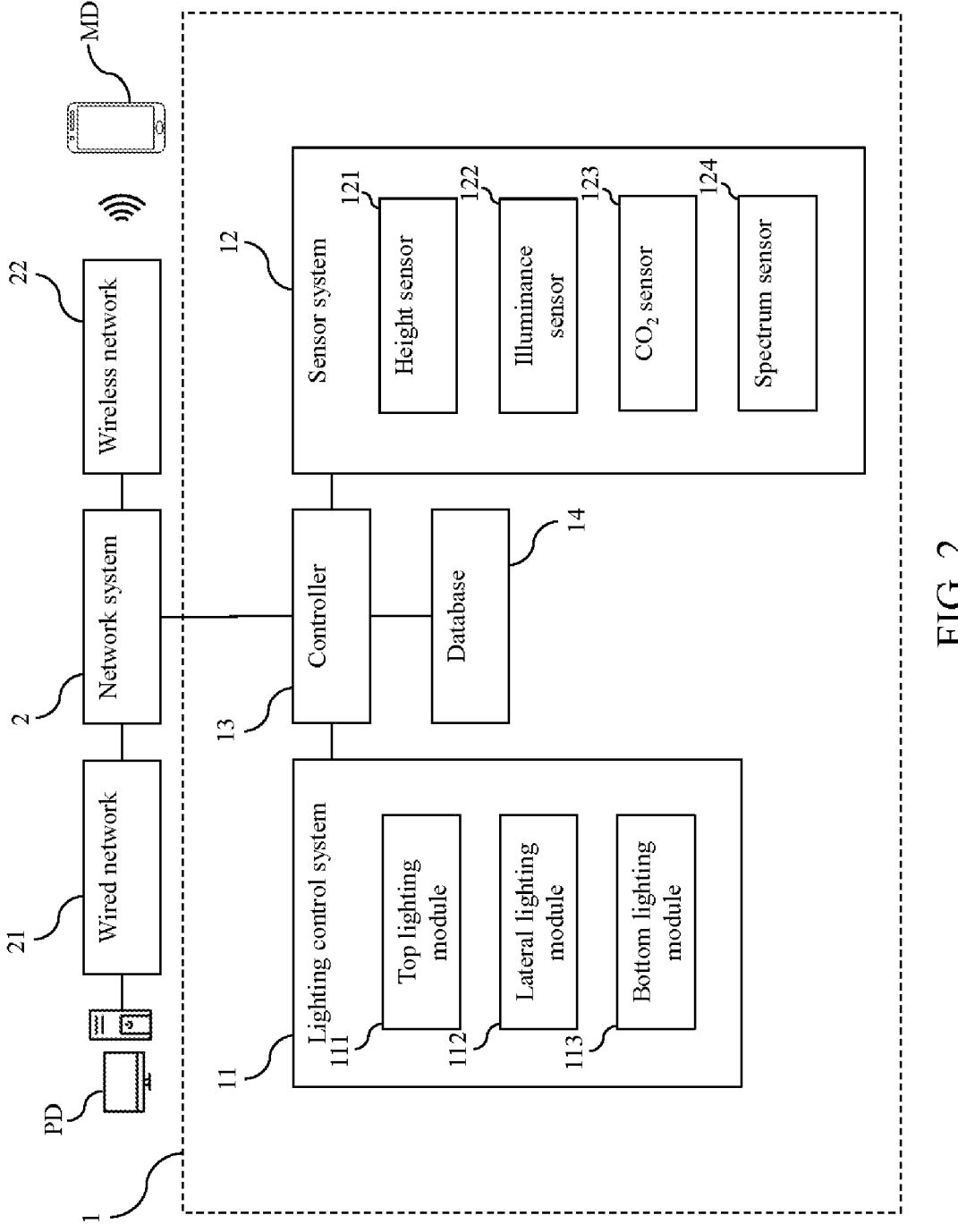
FIG. 2 is a block diagram of the 3D plant growth lighting
system in accordance with one embodiment of the present
invention.

Please refer to FIG. 1 and FIG. 2. FIG. 1 is a schematic
view for illustrating a structure of a three-dimensional (3D)
plant growth lighting system in accordance with one
embodiment of the present invention. FIG. 2 is a block
diagram of the 3D plant growth lighting system in accor-
dance with one embodiment of the present invention. As
shown in FIG. 1 and FIG. 2, the 3D plant growth lighting
system 1 can be installed on a plant chamber GH for
containing plants Pt. The plant chamber GH may be a
greenhouse, a container or other spaces for cultivating
plants. The 3D plant growth lighting system 1 is connected
to a network system 2 with a view to further connecting to
a wired network 21 and a wireless network 22. In one
embodiment, the wired network 22 may be a network based
on Ethernet or other currently available networks; the wire-
less network 22 may be a ZigBee network, a 4G network, a
5G network or other currently available networks. There-
fore, the 3D plant growth lighting system 1 can communi-
cate with the mobile device MD (e.g., a smart phone, a smart
watch, a tablet computer, etc.) or an electronic device LD
(e.g., a personal computer, a laptop computer, etc.) of the
user.

The 3D plant growth lighting system 1 includes a lighting
control system 11, a sensor system 12, a controller 13 and a
database 14. The controller 13 is connected to the lighting
control system 11 and the sensor system 12. In one embodi-
ment, the controller 13 may be a microcontroller unit
(MCU), a central-processing unit (CPU), an application
specific integrated circuit (ASIC), a field programmable gate
array (FPGA) or other similar devices.

The lighting control system 11 includes a plurality of top
lighting modules 111, a plurality of lateral lighting modules
112 and a bottom lighting module 113, which are connected
to the controller 113. The top lighting modules 111 are
disposed on the top of the plant chamber GH and emit lights
toward the bottom of the plant chamber GH. The lateral
lighting modules 112 are disposed on one side of the plant
chamber GH and emit lights toward the other side of the
plant chamber GH. The bottom lighting module 113 is
disposed on the bottom of the plant chamber GH and emits
lights toward the top of the plant chamber GH. In one
embodiment, the top lighting modules 111, lateral lighting
modules 112 and bottom lighting module 113 may be
light-emitting diode (LED) lighting modules or other similar
light sources. The numbers of the top lighting modules 111,
lateral lighting modules 112 and bottom lighting module 113
can be adjusted according to actual requirements. In one
embodiment, the top lighting module 111 may include (but
not limited to) a housing, a plurality of LED light sources
with color temperature of 3000K, a plurality of LED light
sources with color temperature of 5000K and high-power
red light source. Therefore, the top lighting module 111 may
include the light with color temperature of 3000K, the light
with color temperature of 5000K and red light. The ratio of
the light with color temperature of 3000K, the light with
color temperature of 5000K and red light may be 56:8:1, so
the top lighting module 111 can provide the lights having the
wavelengths within a certain range (e.g., 400-700 nm) in
order to effectively promote the growth of the plants Pt. In
one embodiment, the lateral lighting module 112 may
include (but not limited to) a tubular housing, a light source
substrate and a plurality of LED light source having three
chips (which may include a red light chip, a blue light chip
and a white light chip). In one embodiment, the bottom
lighting module 113 may include (but not limited to) a
tubular housing, a light source substrate, a plurality of white
light bicolor-packaging LED light source and a high-power blue light source. The bottom lighting module 111 may include white light, red light and purple light, and the ratio of white light, red light and purple light may be 7:1:1. The special light ratio provided by the 3D lighting structure formed by the top lighting modules 111, lateral lighting modules 112 and bottom lighting module 113 can conform to the growth requirements of most plants. Thus, the 3D plant growth lighting system 1 can effectively promote the growth of the plants Pt.

As set forth above, the 3D plant growth lighting system 1 has the top lighting modules 111, lateral lighting modules 112 and bottom lighting module 113. The lights emitted by the 3D lighting structure formed by the above lighting modules can irradiate the front sides, backs sides and stems of the leaves of the plants Pt. In addition, the lights emitted by these lighting modules can also irradiate most of the leaves of the plants Pt. Therefore, the 3D plant growth lighting system 1 can optimize the photosynthesis of the plants Pt with a view to effectively promote the growth of the plants Pt.

The sensor system 12 includes a height sensor 121, an illuminance sensor 122, a carbon dioxide (CO2) module 123 and a spectrum sensor 124, which are connected to the controller 13. The height sensor 121 detects the height of the plants Pt to generate a height signal. The illuminance sensor 122 detects the illuminance of the plant chamber GH to generate an illuminance signal. The CO2 module 123 includes a carbon dioxide (CO2) sensor 1231 and a carbon dioxide (CO2) generator 1232. The CO2 sensor 1231 detects the CO2 concentration of the plant chamber GH to generate a CO2 concentration signal. When the controller 13 determines that the CO2 concentration of the plant chamber GH is insufficient, the controller 13 controls the CO2 generator 1232 to generate CO2. The spectrum sensor 124 detects the spectrums of the lights in the plant chamber GH to generate a spectrum signal. In one embodiment, the height sensor 121 may be an infrared sensor, a laser sensor or other similar components. The controller 13 can perform adjustments according to the height signal, illuminance signal and spectrum signal so as to satisfy the growth requirements of the plants Pt.

The embodiment just exemplifies the present invention and is not intended to limit the scope of the present invention; any equivalent modification and variation according to the spirit of the present invention is to be also included within the scope of the following claims and their equivalents.

Figure 3A:
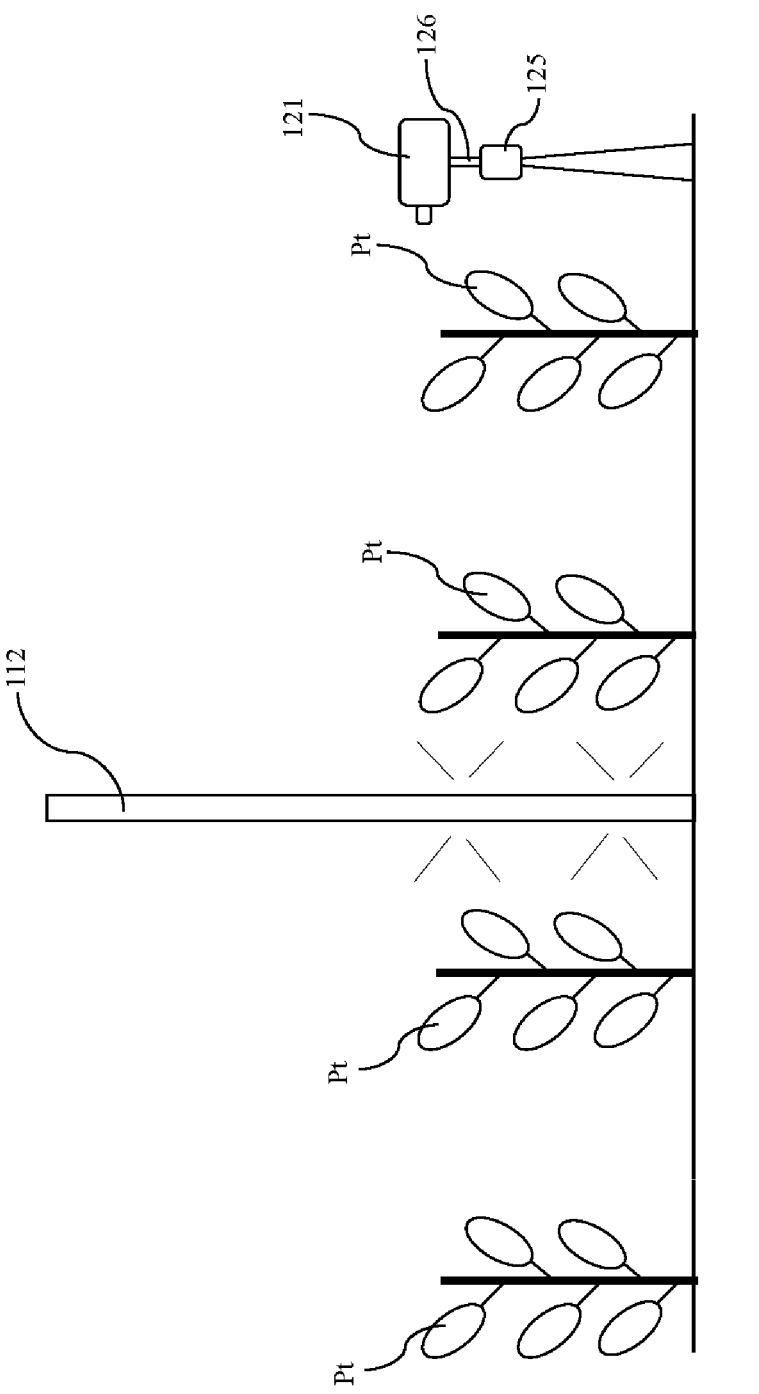
FIG. 3A is a first schematic view for illustrating an
operational mechanism of a height sensor of the 3D plant
growth lighting system in accordance with one embodiment
of the present invention.
Figure 3B:
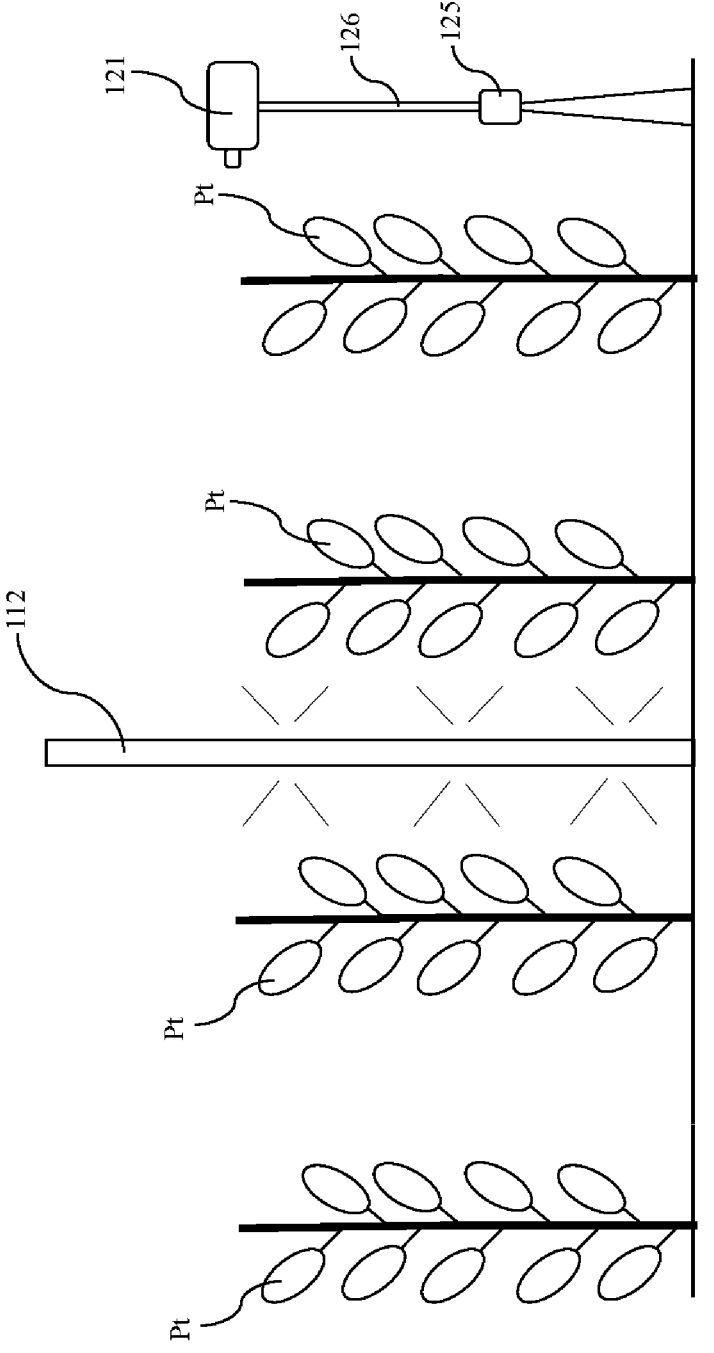
FIG. 3B is a second schematic view for illustrating the
operational mechanism of the height sensor of the 3D plant
growth lighting system in accordance with one embodiment
of the present invention.
Figure 3C:
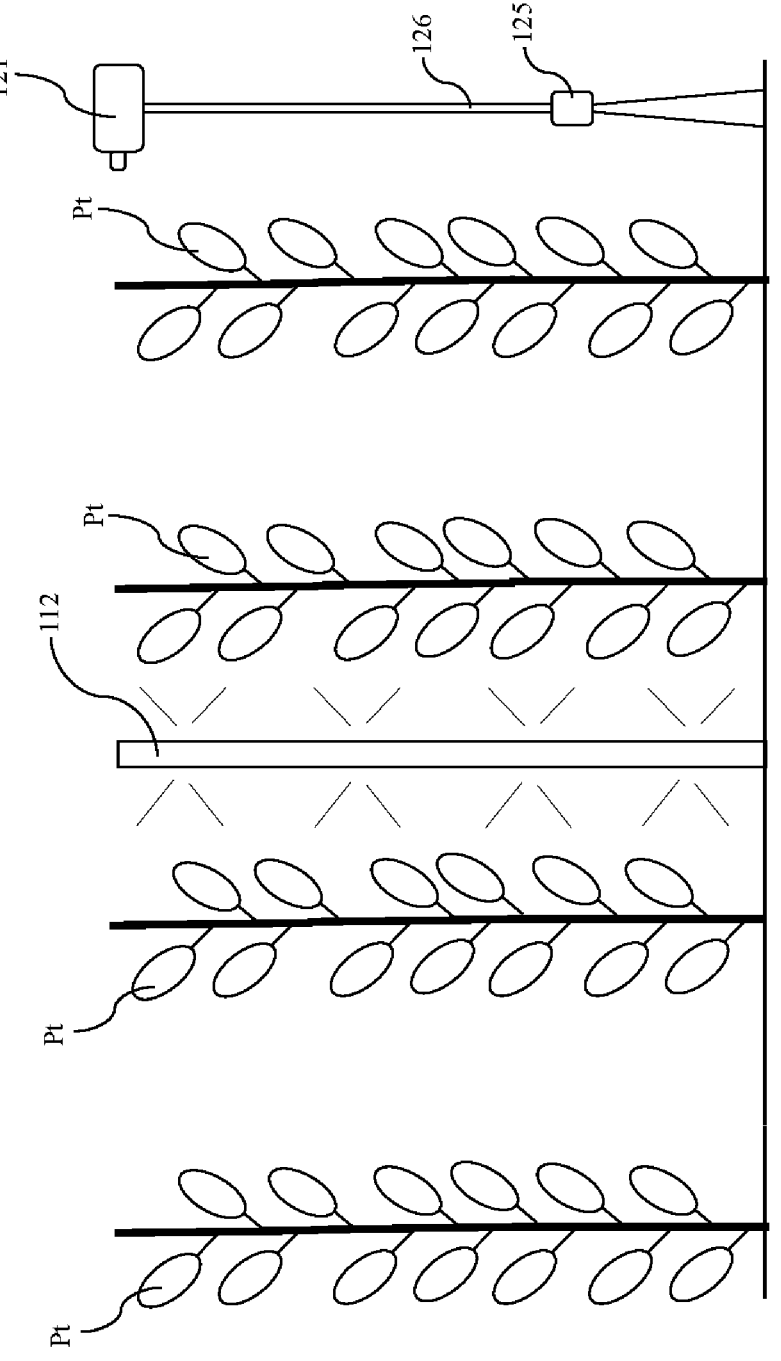
FIG. 3C is a third schematic view for illustrating the
operational mechanism of the height sensor of the 3D plant
growth lighting system in accordance with one embodiment
of the present invention.

Please refer to FIG. 3A~FIG. 3B. FIG. 3A is a first schematic view for illustrating an operational mechanism of a height sensor of the 3D plant growth lighting system in accordance with one embodiment of the present invention. FIG. 3B is a second schematic view for illustrating the operational mechanism of the height sensor of the 3D plant growth lighting system in accordance with one embodiment of the present invention. FIG. 3C is a third schematic view for illustrating the operational mechanism of the height sensor of the 3D plant growth lighting system in accordance with one embodiment of the present invention. As shown in FIG. 3A, the sensor system 12 further includes a motor module 125 and a lifting mechanism 126. The motor module 125 is connected to the lifting mechanism 126 and controller 13. The height sensor 121 is disposed on the lifting mechanism 126, such that the height sensor 121 can detect the height of the plants Pt to generate the height signal.

As shown in FIG. 3B, when the plants Pt keep growing, the height of the plants Pt change. The controller 14 can control the lifting mechanism 126 to adjust the height of the height sensor 121 and adjust the lighting range of the lateral lighting modules 112 in order to increase the lighting range of the lateral lighting modules 112.

As shown in FIG. 3C, the controller 13 continuously adjusts the lighting range of the lateral lighting modules 112 according to the height signal, such that the lighting range of the lateral lighting modules 112 can be changed according to the height of the plants Pt. The above mechanism not only can effectively enhance the effect of photosynthesize, but also can save more energy.

As described above, the database 14 is connected to the controller 13. The database 14 can save a plurality of light formulas. The above light formulas are corresponding to a plurality of plant species. Each light formula can further include the light formula information of each of the growth stages of each plant species.

The above light formulas can be obtained by Big Data analysis. The user can download these light formulas from the network system 2 (the wired network 21 or wireless network 22) by his/her mobile device MD or electronic device LD, and these light formulas can be saved in the database 14. Then, the user can select the light formula corresponding to the species of the plants Pt, and the controller 13 can compare the illuminance signal, CO2 concentration signal and spectrum signal with the light formula so as to obtain an illuminance comparison result, a CO2 concentration comparison result and a spectrum comparison result. Afterward, the controller 13 generates an intelligent control signal according to these comparison results so as to adjust the lighting control system 11 and the CO2 generator 1232, which can adjust the environment of the plant chamber GH. As a result, the environment created by the 3D plant growth lighting system 1 can satisfy the growth requirements of the plants Pt.

Therefore, each of the light formulas saved in the database 14 of the 3D plant growth lighting system 1 is corresponding to one plant species, and includes the illuminance parameters, spectrum parameters and CO2 concentration parameters. Thus, the controller 13 not only can precisely adjust the lights emitted by the top lighting modules 111, lateral lighting modules 112 and bottom lighting module 113, but also can adjust the CO2 generated by the CO2 generator. Accordingly, the environment created by the 3D plant growth lighting system 1 can definitely meet the requirements of different growth stages of the plants Pt.

The embodiment just exemplifies the present invention and is not intended to limit the scope of the present invention; any equivalent modification and variation according to the spirit of the present invention is to be also included within the scope of the following claims and their equivalents.

It is worthy to point out that the lighting devices of a currently available plant growth lighting system are arranged above the plants. The lights emitted by the lighting devices of the plant growth lighting system cannot irradiate the back sides of leaves and stems of the plants. In addition, the lights emitted by the lighting devices of the plant growth lighting system can only irradiate the leaves on the top of the plants, while other leaves blocked by the top leaves of the plants cannot effectively photosynthesize. Therefore, the currently available plant growth lighting system cannot effectively optimize the effect of photosynthesis. On the contrary, according to one embodiment of the present invention, the 3D plant growth lighting system has a top lighting module, a lateral lighting module and a bottom lighting module. The lights emitted by the above three lighting modules can irradiate the front sides, the back sides and the stems of the plant. Thus, the 3D plant growth lighting system can effectively enhance the photosynthesis of the plant in order to optimize the effect of photosynthesis.

Also, according to one embodiment of the present invention, the 3D plant growth lighting system has the top lighting module, the lateral lighting module and the bottom lighting module. The lights emitted by the above three lighting modules can irradiate most of the leaves of the plant. Therefore, the 3D plant growth lighting system can further enhance the photosynthesis of the plant so order to further optimize the effect of photosynthesis.

Further, according to one embodiment of the present invention, the 3D plant growth lighting system includes a motor module, a lifting mechanism and a height sensor. The height sensor can detect the height of the plant in order to generate a height signal. In this way, the controller can control the lifting mechanism to adjust the height of the height sensor and the lighting range of the lateral lighting module according to the height signal. Accordingly, the lighting range of the lateral lighting module can be changed according to the height of the plant, which not only can further optimize the effect of the photosynthesis, but also can save more energy.

Moreover, according to one embodiment of the present invention, the 3D plant growth lighting system includes a database saving a plurality of light formulas. Each light formula is corresponding to one plant species, so the light formula can satisfy the growth requirements of the plant. Thus, the controller not only can adjust the brightness, spectrum and color temperature of each of the top lighting module, lateral lighting module and bottom lighting module according to the light formula, but also can adjust the $CO_2$ concentration according to the light formula. In this way, the 3D plant growth lighting system can create an environment capable of satisfying the growth requirements of the plant.

Furthermore, according to one embodiment of the present invention, the 3D plant growth lighting system includes the database saving the light formulas. Each light formula is corresponding to one plant species, and includes the illuminance parameters, spectrum parameters and $CO_2$ concentration parameters of different growth stages of the plant. Accordingly, the controller not only can precisely adjust the lights emitted by the top lighting module, lateral lighting module and the bottom lighting module, but also can accurately adjust the $CO_2$ generated by the $CO_2$ generator. As a result, the environment created by the plant growth lighting system can completely conform to the requirements of different growth stages of the plant. As described above, the 3D plant growth lighting system can definitely achieve great technical effects.

Figure 4:
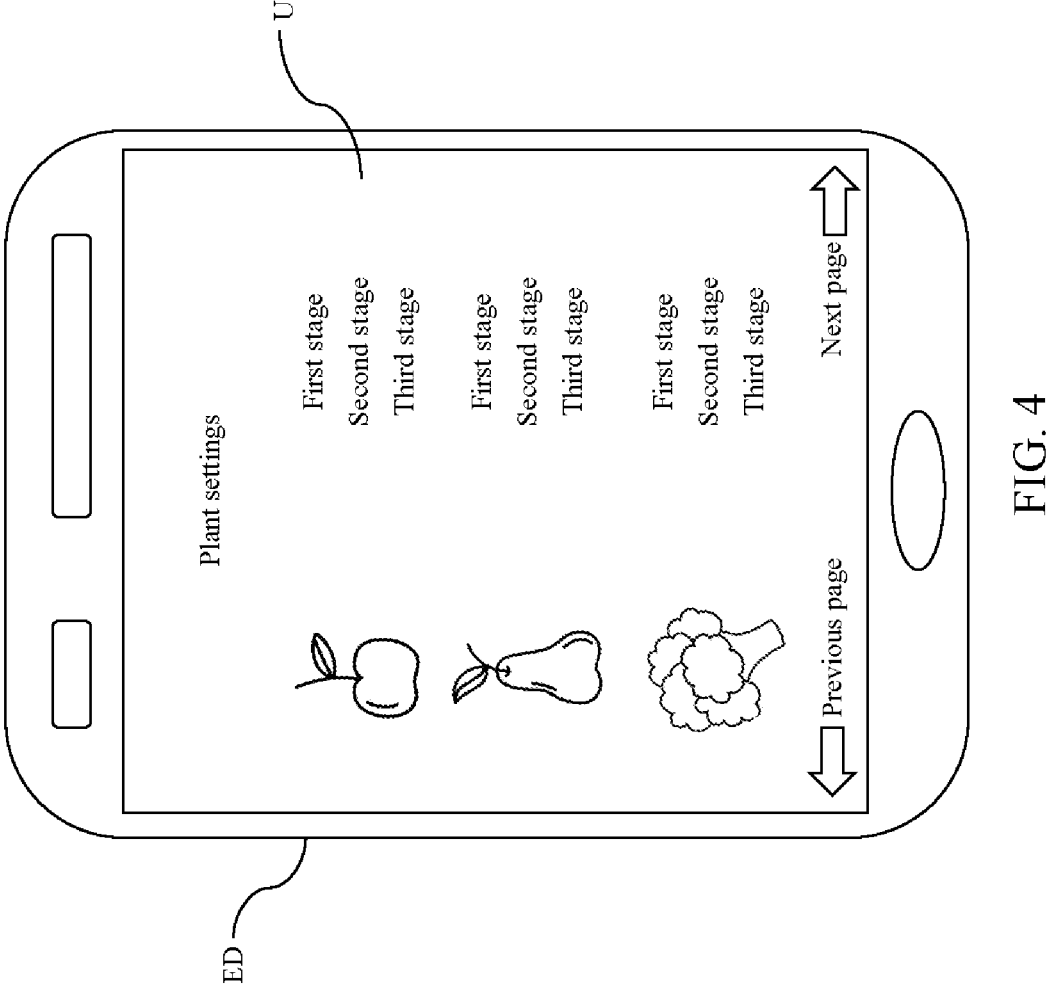
FIG. 4 is a schematic view for illustrating a user interface
of an application of the 3D plant growth lighting system in
accordance with one embodiment of the present invention.

Please refer to FIG. 4, which is a schematic view for illustrating a user interface of an application of the 3D plant growth lighting system in accordance with one embodiment of the present invention. As shown in FIG. 4, the user can download the application of the 3D plant growth lighting system 1 by his/her mobile device MD so as to interact with the 3D plant growth lighting system 1. The application can provide a user interface UF for the user, which includes a plurality of light formulas corresponding to several plant species respectively. In addition, the user can select one plant species and one of the growth stages of the plant species via the user interface UF. The growth stages may be a first stage, a second stage and a third stage (e.g., an initial stage, a middle stage and a final stage). The user can select the plant species corresponding to the plants Pt and the current growth stage of the plants Pt via the user interface UF. Therefore, the controller 13 can generate an intelligent control signal according to the selection result of the user to adjust the lighting control system 11 and $CO_2$ generator 1232 with an eye to optimizing the growth environment of the plants Pt.

The embodiment just exemplifies the present invention and is not intended to limit the scope of the present invention; any equivalent modification and variation according to the spirit of the present invention is to be also included within the scope of the following claims and their equivalents.

Figure 5:
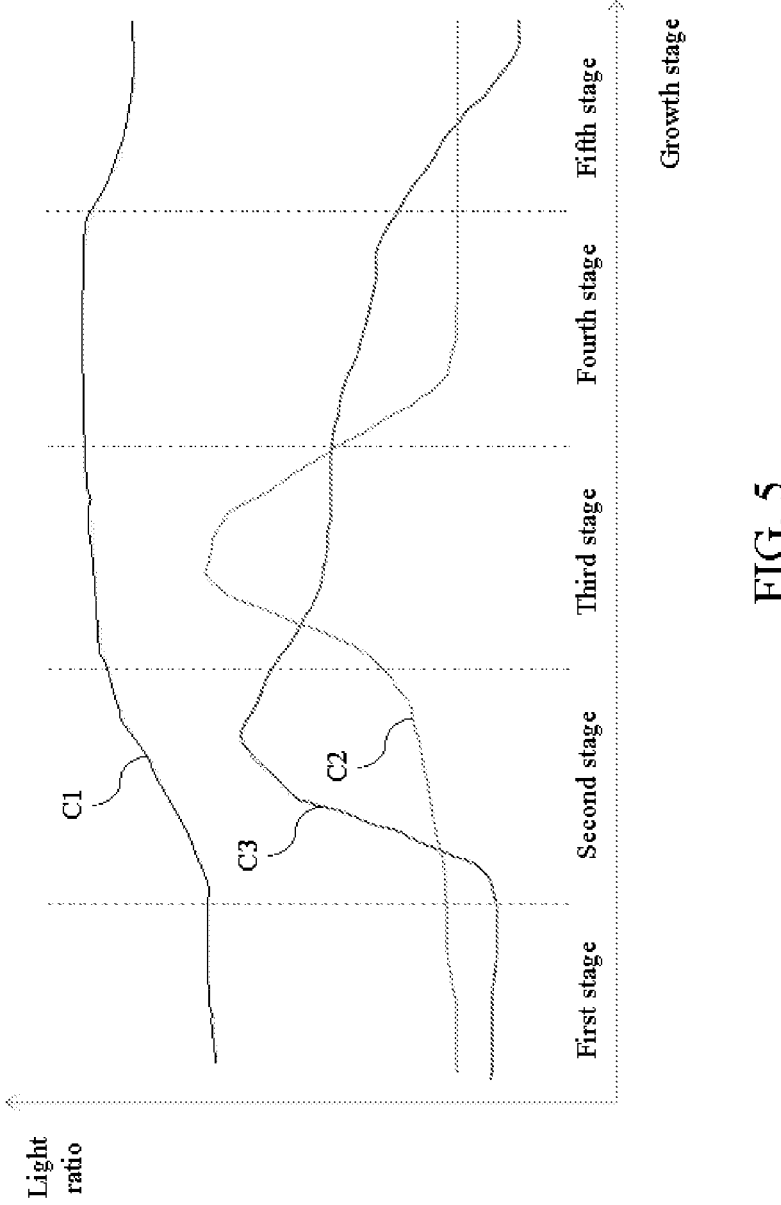
FIG. 5 is a schematic view for illustrating a light ratio of
a lighting control system of the 3D plant growth lighting
system in accordance with one embodiment of the present
invention.

Please refer to FIG. 5, which is a schematic view for illustrating a light ratio of a lighting control system of the 3D plant growth lighting system in accordance with one embodiment of the present invention. As shown in FIG. 5, the curve C1 stands for white light; the curve C2 stands for blue light; the curve C3 stands for purple light. In this embodiment, the light formula can divide the growth process of one plant species into five stages, such as a first stage, a second stage, a third stage, a fourth stage and a fifth stage. The first stage may be a seedling stage; the second stage may be a growing-tall stage; the third stage may be a leaves-growing stage; the fourth stage may be a flowering stage; the fifth stage may be a fruit-bearing stage. The controller 13 can adjust light ratio of the lighting control system 11 according to the current growth stage of the plants Pt.

In the first stage, the controller 13 adjusts the light ratio of the lighting control system 11 to make the content of the white light be greater than the contents of the blue light and purple light. Besides, the contents of the white light, blue light and purple light substantially remain unchanged in the first stage.

In the second stage, the controller 13 adjusts the light ratio of the lighting control system 11 to make the content of the white light be greater than the contents of the blue light and purple light. Besides, the controller 13 gradually increases the contents of the white light and blue light. In addition, the controller 13 significantly increases the content of the purple light in order to make the content of the purple light be greater than that of the blue light.

In the third stage, the controller 13 adjusts the light ratio of the lighting control system 11 to make the content of the white light be greater than the contents of the blue light and purple light. Besides, the controller 13 gradually reduces the content of the purple light. Further, the controller 13 increases the content of the blue light first and then reduces the content of the blue light, such that the content of the blue light is greater than that of the purple light during most of the third stage.

In the fourth stage, the controller 13 adjusts the light ratio of the lighting control system 11 to make the content of the white light be greater than the content of the purple light. Besides, the controller 13 gradually reduces the content of the purple light and significantly decreases the content of the purple light, such that the content of the purple light is greater than that of the blue light during the fourth stage. The content of the white light substantially remains unchanged during the fourth stage.

In the fifth stage, the controller 13 adjusts the light ratio of the lighting control system 11 to make the content of the white light be greater than the contents of the blue light and purple light. Besides, the controller 13 gradually reduces the content of the white light and significantly decreases the content of the purple light. Thus, the content of the blue light is greater than that of the purple light during the last half of the fifth stage. The content of the blue light substantially remains unchanged during the fifth stage.

As set forth above, the 3D plant growth lighting system 1 can adjust the light ratio of the lights emitted by the top lighting modules 111, lateral lighting modules 112 and bottom lighting module 113 according to the light formula so as to conform to the requirements of all growth stages of the plants Pt. Therefore, the 3D plant growth lighting system 1 can effectively promote the growth of the plants Pt.

The embodiment just exemplifies the present invention and is not intended to limit the scope of the present invention; any equivalent modification and variation according to the spirit of the present invention is to be also included within the scope of the following claims and their equivalents.

To sum up, according to one embodiment of the present invention, the 3D plant growth lighting system has a top lighting module, a lateral lighting module and a bottom lighting module. The lights emitted by the above three lighting modules can irradiate the front sides, the back sides and the stems of the plant. Thus, the 3D plant growth lighting system can effectively enhance the photosynthesis of the plant in order to optimize the effect of photosynthesis.

Also, according to one embodiment of the present invention, the 3D plant growth lighting system has the top lighting module, the lateral lighting module and the bottom lighting module. The lights emitted by the above three lighting modules can irradiate most of the leaves of the plant. Therefore, the 3D plant growth lighting system can further enhance the photosynthesis of the plant so order to further optimize the effect of photosynthesis.

Further, according to one embodiment of the present invention, the 3D plant growth lighting system includes a motor module, a lifting mechanism and a height sensor. The height sensor can detect the height of the plant in order to generate a height signal. In this way, the controller can control the lifting mechanism to adjust the height of the height sensor and the lighting range of the lateral lighting module according to the height signal. Accordingly, the lighting range of the lateral lighting module can be changed according to the height of the plant, which not only can further optimize the effect of the photosynthesis, but also can save more energy.

Moreover, according to one embodiment of the present invention, the 3D plant growth lighting system includes a database saving a plurality of light formulas. Each light formula is corresponding to one plant species, so the light formula can satisfy the growth requirements of the plant. Thus, the controller not only can adjust the brightness, spectrum and color temperature of each of the top lighting module, lateral lighting module and bottom lighting module according to the light formula, but also can adjust the CO2 concentration according to the light formula. In this way, the 3D plant growth lighting system can create an environment capable of satisfying the growth requirements of the plant.

Furthermore, according to one embodiment of the present invention, the 3D plant growth lighting system includes the database saving the light formulas. Each light formula is corresponding to one plant species, and includes the illuminance parameters, spectrum parameters and CO2 concentration parameters of different growth stages of the plant. Accordingly, the controller not only can precisely adjust the lights emitted by the top lighting module, lateral lighting module and the bottom lighting module, but also can accurately adjust the CO2 generated by the CO2 generator. As a result, the environment created by the plant growth lighting system can completely conform to the requirements of different growth stages of the plant.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A three-dimensional (3D) plant growth lighting system, comprising:

a top lighting module disposed on a top of a plant chamber, wherein the plant chamber contains a plant;

a lateral lighting module disposed on one side of the plant chamber;

a bottom lighting module disposed on a bottom of the plant chamber;

a controller connected to the top lighting module, the lateral lighting module and the bottom lighting module so as to control the top lighting module, the lateral lighting module and the bottom lighting module;

a database connected to the controller and configured to save a plurality of light formulas corresponding to a plurality of plant species respectively;

a carbon dioxide module connected to the controller, and comprising a carbon dioxide generator and a carbon dioxide sensor configured to detect a carbon dioxide concentration of the plant chamber and generate a carbon dioxide concentration signal;

an illuminance sensor connected to the controller and configured to detect an illuminance of the plant chamber in order to generate an illuminance signal; and a spectrum sensor connected to the controller and configured to detect a spectrum of a light in the plant chamber so as to generate a spectrum signal;

wherein the controller is configured to download the light formula corresponding to the plant from the database, and compare the light formula with the carbon dioxide concentration signal, the illuminance signal and the spectrum signal to generate an intelligent control signal so as to control one or more of the carbon dioxide generator, the top lighting module, the lateral lighting module and the bottom lighting module.

2. The 3D plant growth lighting system as claimed in claim 1, further comprising a height sensor connected to the controller, wherein the height sensor is configured to detect a height of the plant in order to generate a height signal and the controller adjusts a lighting range of the lateral lighting module according to the height signal.

3. The 3D plant growth lighting system as claimed in claim 1, wherein the controller is configured to download the light formula corresponding to the plant from the database and generate an intelligent control signal according to the light formula in order to control the top lighting module, the lateral lighting module and the bottom lighting module.

4. The 3D plant growth lighting system as claimed in claim 1, wherein the controller is configured to control the carbon dioxide generator according to the carbon dioxide concentration signal.

5. The 3D plant growth lighting system as claimed in claim 1, wherein the top lighting module, the lateral lighting module and the bottom lighting module are light-emitting diode lighting modules.

\* \* \* \* \*